US006168798B1

(12) United States Patent
O'Halloran et al.

(10) Patent No.: US 6,168,798 B1
(45) Date of Patent: Jan. 2, 2001

(54) NON-IRRITATING COMPOSITION FOR TREATING ACNE AND OTHER SKIN CONDITIONS

(75) Inventors: David P. O'Halloran, Milltown; Deborah Rudtke, Hillsdale; Joyce Mayes-Smith, North Brunswick, all of NJ (US)

(73) Assignee: Bristol-Myers Squibb Company, New York, NY (US)

( * ) Notice: Under 35 U.S.C. 154(b), the term of this patent shall be extended for 0 days.

(21) Appl. No.: 08/792,999

(22) Filed: Feb. 3, 1997

(51) Int. Cl.[7] .................................................. A61K 7/48

(52) U.S. Cl. .......................... 424/401; 514/159; 514/844; 514/859

(58) Field of Search ............................ 424/401; 514/844, 514/859, 159

(56) References Cited

U.S. PATENT DOCUMENTS

| | | | | |
|---|---|---|---|---|
| 4,275,222 | | 6/1981 | Scala, Jr. . | |
| 4,743,442 | * | 5/1988 | Raaf | 424/47 |
| 4,800,197 | * | 1/1989 | Kowcz et al. | 514/162 |
| 5,382,432 | * | 1/1995 | McCook et al. | 424/401 |
| 5,409,705 | * | 4/1995 | Kitz | 424/401 |
| 5,466,680 | | 11/1995 | Rudy . | |
| 5,516,793 | * | 5/1996 | Duffy | 514/474 |
| 5,567,427 | * | 10/1996 | Papadakis | 424/401 |
| 5,607,921 | * | 3/1997 | Bernard et al. | 514/23 |
| 5,609,875 | * | 3/1997 | Hadas | 424/195.1 |
| 5,626,868 | * | 5/1997 | Morancais et al. | 424/450 |
| 5,716,625 | * | 2/1998 | Hahn et al. | 424/401 |

FOREIGN PATENT DOCUMENTS

| | | | |
|---|---|---|---|
| 195 03 423 | | 8/1996 | (DE) . |
| 241818 A2 | * | 10/1987 | (EP) . |
| 2250813 A2 | | 10/1990 | (JP) . |
| WO 96/18184 | | 6/1996 | (WO) . |
| WO 96/19181 | | 6/1996 | (WO) . |
| WO 96/19182 | | 6/1996 | (WO) . |
| WO 96/19183 | | 6/1996 | (WO) . |
| WO 96/19228 | | 6/1996 | (WO) . |
| 96192281 | * | 6/1996 | (WO) . |

OTHER PUBLICATIONS

Chemical Abstracts, 125:123723.*
Chemical Abstracts, 125:150778.*
Chemical Abstracts, 125:150779*
Chemical Abstracts, 125:150780.*
Chemical Abstracts, 125:150781.*
Chemical Abstracts, 128:106418.*

* cited by examiner

*Primary Examiner*—Robert H. Harrison
(74) *Attorney, Agent, or Firm*—Charles J. Zeller

(57) ABSTRACT

The invention provides methods and compositions which are mild and nonirritating for reducing and eliminating skin disorders, particularly blemishes and redness associated with acne. The hydroalcoholic compositions of the invention contain a keratolytic compound, preferably a β-hydroxy carboxylic acid, more preferably salicylic acid or pharmaceutically acceptable salt thereof; and a glycerophosphate ester or salt, formulated with pharmaceutically acceptable carriers. Preferred glycerophosphate salts for use in the methods and compositions of the invention are sodium glycerophosphate and calcium glycerophosphate. Additional anti-irritancy agents are not required in the compositions of the present invention, as the glycerophosphate salt component uniquely endows the compositions with nonirritant properties. Other components which may be formulated into the compositions of the invention include fragrances, colorants, emollients, humectants and antimicrobial agents.

25 Claims, 1 Drawing Sheet

% OF CONTROL
140
120
100
80
60
40
20
0
1
4
8
16
EXPOSURE TIME (HOURS)

NON-IRRITATING COMPOSITION FOR TREATING ACNE AND OTHER SKIN CONDITIONS

FIELD OF THE INVENTION

The invention relates generally to compositions and methods for topical application to the skin to treat conditions, such as acne, which often cause blemishes, pimples and redness.

BACKGROUND OF THE INVENTION

Aging, hormonal changes, and approaching adolescence often cause unsightly and embarrassing skin conditions which take the form of pimples, blemishes, pustules and reddened areas. These skin problems take their toll not only in emotional anxiety and distress but also in physical marring of the skin, sometimes associated with pain, in both juveniles and adults. Age-related skin problems can arise either from disease or illness, or as a consequence of hormonal changes. Skin problems can be exacerbated by environmental influences such as, for example, improper diet, stress or tension, and lack of sleep. Disease conditions include dry skin, ichthyosis, eczema, palmar and plantar hyperkeratoses, dandruff, acne and warts. Skin changes associated with aging can result in such symptoms as age spots, wrinkling and related aging changes.

A number of issued patents disclose the use of α-hydroxy acids and salts such as lactic and glycolic acids, for the treatment of diseased and nondiseased skin and wrinkles (U.S. Pat. Nos. 4,105,782, 4,105,783, 4,021,572, 3,879,537, 3,920,835, 3,984,566 and 3,988,470 to Van Scott and Yu and U.S. Pat. No. 5,091,171 to Yu et al.). These patents focus primarily on α-hydroxy acids of lower molecular weight. Ammonium salts were found to be more effective than the free acid, and both of the aforementioned forms were said to be substantially better than the alkali metal salts. A problem with the use of these compounds is that the levels at which the α-hydroxy acids are most effective in commercial products results in a stinging sensation and even redness after application on the skin. Indeed, the stinging and redness is reputed to be an indication to the user that the product is working. However, those who use products containing α-hydroxy acids and salts and apply them to their skin would rather have performance without such side effects.

Compositions and methods for the treatment of acne vulgaris are disclosed in U.S. Pat. No. 4,536,399 to Flynn et al., which describes the combination of benzoyl peroxide or salicylic acid with fumed silica intended to treat oily skin. Benzoyl peroxide based anti-acne compositions with irritation suppressants are described in U.S. Pat. No. 4,545,990 to Le Poyer de Cosul et al. U.S. Pat. No. 4,608,370 to Aronsohn describes the removal of at least some blemishes and the imparting of a useful, healthy complexion with a composition of salicylic acid, resorcinol, lactic acid and ethyl alcohol. U.S. Pat. No. 5,482,710 to Slavtcheff et al. discloses cosmetic compositions which include at least one keratolytic agent (e.g., the β- and α-hydroxy carboxylic acids, e.g., salicylic acid and glycolic or lactic acid) and a combination of water soluble and water insoluble anti-irritancy agents, such as a salt of glycyrrhizinic acid and α-bisabolol, respectively). Other anti-acne treatments are reported in U.S. Pat. Nos. 4,613,592 and 4,772,592 to Benzoni. These treatments utilize $C_1$–$C_4$ alkyl lactates as the active ingredient in a water-in-oil emulsion.

U.S. Pat. No. 5,057,502 to Walsh describes the use of Juniper extract materials to reduce thin heavy oily, greasy secretions from the skin. Co-actives are reported to be vitamin A, aloe vera and camomile extract. Pulverized flowers are reported in the skin treatments of U.S. Pat. Nos. 4,880,621 and 4,933,177 to Grollier et al. Although many of the above-described treatment compositions and methods may prove useful, they suffer from slow performance and/or unsatisfactory results, or have unacceptable qualities, as perceived by the user.

Thus, it is clear that the art is in need of cosmetic formulations and compositions to reduce or eliminate skin conditions, such as blemishes and redness, without producing irritation, stinging, or further redness to the skin. The formulations should work to mitigate such skin conditions within a short time period after application. The formulations should provide a good feeling to the user after application and, ideally, should control sebum production and should not leave the skin looking shiny after application. Further, the formulations should not deposit a greasy or oily film or residue on the skin surface.

SUMMARY OF THE INVENTION

The present invention provides a cosmetic composition for application on the skin for reducing and eliminating skin conditions, such as acne and its associated blemishes and redness. It is an object of the present invention to provide stable and nonirritating formulations for cosmetic use that function to reduce and eliminate pimples, blemishes and redness within a short period of time after topical application. More particularly, an object of the invention is to provide a non-irritating anti-acne astringent for topical application on the skin which contains component ingredients which reduce and/or alleviate irritation and burning sensations on the skin.

It is another object of the present invention to provide a clear, hydroalcoholic cosmetic composition containing a $C_2$–$C_{18}$ polyhydric alcohol phosphate ester, a disaccharide polyol phosphate ester, or said esters as a salt complex of a mono- or divalent metal ion for the treatment of pimples, blemishes and redness which feels comfortable and clean to the user after application and which avoids undesirable side effects such as stinging, burning, and brightened skin color.

It is also an object of the invention to avoid greasy or oily residues on the skin after application of the cosmetic compositions described herein. In accordance with the invention, the compositions optimally dry quickly and cleanly (without visible residue or stickiness) after application on the skin.

It is yet another object of the invention to provide effective anti-acne formulations which are milder than other compositions in the art, which actively mitigate skin conditions for which they are being used, and which substantially alleviate or minimize stinging or burning sensation upon or after application on the skin of the user.

It is still yet another object of the invention to provide methods for reducing skin irritation after topical application of an anti-acne or skin treatment composition by applying the above-mentioned non-irritating compositions formulated in accordance with the invention.

Further objects and advantages afforded by the invention will be apparent from the detailed description hereinbelow.

DESCRIPTION OF THE DRAWINGS

The appended drawings of the figures are presented to further describe the invention and to assist in its understanding through clarification of its various aspects.

DETAILED DESCRIPTION OF THE INVENTION

Figure 1:
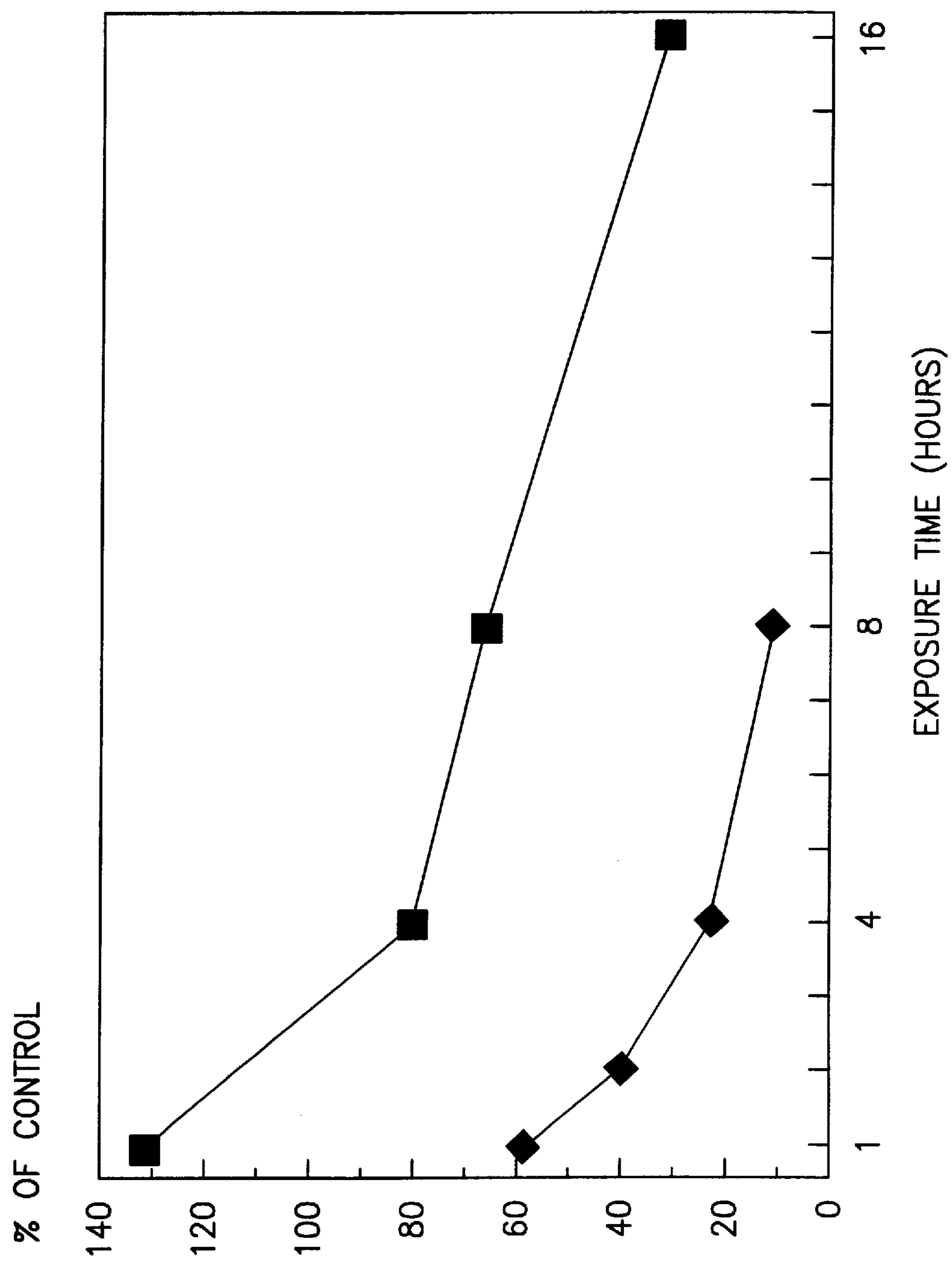
FIG. 1 shows the exposure time results of the MTT Epiderm™ skin model bioassay (Example 3) comparing the properties of the composition formulated in accordance with the invention (closed squares) with those of a commercially-available hydroalcoholic product containing 0.5% salicylic acid, hereinafter identified as "the comparative product" (closed diamonds).

The present invention provides cosmetic compositions or astringents for reducing and/or eliminating skin conditions, such as acne, on the skin via topical application on the desired site. The invention further provides such compositions formulated as pharmaceutically acceptable compositions for topical application to human tissues for the purpose of improving and alleviating adverse skin conditions, such as pimples, blemishes and redness. The compositions of the invention provide advantages to the art in that they exhibit less irritation and are significantly milder upon application and use than commercially-available astringent products for skin conditions. Moreover, as hydroalcoholic formulations, the compositions are quick-drying and non-sticky after application on the skin.

The cosmetic compositions of the present invention are preferably formulated as aqueous, hydroalcoholic solutions with no precipitate. A clear solution is preferred. The essential components in the composition of the present invention are alcohol, water, at least one keratolytic agent, preferably a β-hydroxy carboxylic acid or cosmetically acceptable salt thereof, e.g., salicylic acid or sodium salicylate; and at least one polyhydric alcohol phosphate ester, a disaccharide polyol phosphate ester, or said esters as a salt complex of a mono- or divalent metal ion preferably sodium, potassium, ammonium, magnesium or calcium, e.g., calcium glycerophosphate. All of the essential components of the present compositions are optimally water soluble.

$C_3$–$C_{15}$ β-hydroxy carboxylic acids, preferably $C_3$–$C_{10}$ β-hydroxy carboxylic acids, or cosmetically-acceptable salts thereof, are suitable for use in accordance with the present invention. These acids function as anti-acne actives in the compositions. Examples of $C_3$–$C_{10}$ β-hydroxy carboxylic acids for use in the invention include, but are not limited to, the active forms of glyceric acid, α,β-dihydroxypropionic acid, β-hydroxy butyric acid, β-hydroxy pentanoic acid, β-hydroxy glutamic acid, β-hydroxy hexanoic acid, β-hydroxy benzoic acid (salicylic acid), β-hydroxy heptanoic acid, β-hydroxy octanoic acid, β-hydroxy nonanoic acid, β-hydroxy decanoic acid, β-hydroxy undecanoic acid and β-hydroxy dodecanoic acid. A preferred β-hydroxy carboxylic acid for the present invention is salicylic acid or a cosmetically acceptable salt thereof, i.e., sodium salicylate.

The $C_2$–$C_{18}$ polyhydric alcohol phosphate or disaccharide polyol phosphate salts complexed to a mono- or divalent metal ion for use in the present compositions include, but are not limited to, ethoxydiglycol phosphate salts, sorbitol phosphate salts, mannitol phosphate salts, maltitol phosphate salts and glycerophosphate salts. The metal ions include, but are not limited to, sodium, potassium, ammonium, magnesium and calcium, with calcium preferred. Preferred as a component in the present compositions is a glycerophosphate ester or salt, such as calcium glycerophosphate.

Suitable glycerophosphate salts to include in the compositions of the present invention, e.g., sodium, potassium, ammonium and calcium glycerophosphates, are commercially available from Seppic SA, France. A preferred glycerophosphate salt with a monovalent cation is sodium glycerophosphate; a preferred glycerophosphate salt with a divalent cation is calcium glycerophosphate, including its α and β forms (International Cosmetic Ingredient Handbook, Third Edition, *Monographs,* Eds. J. A. Wenninger and G. N. McEwen. Jr., Ph.D. J. D., *The Cosmetic, Toiletry and Fragrance Association*, Washington, D.C., page 91, 1995; International Cosmetic Ingredient Dictionary, Sixth Edition, Ibid., page 126; Merck Index, Compound No. 1644, 10th Ed., 1983, page 1656).

Alcohol is present in the present composition in an amount of from about 5% to 55%, preferably, about 15% to 40%, more preferably, about 25% to 40%, by weight. Water is present at about 50% to 95%, preferably about 60% to 80%, more preferably, about 65% to 75%, by weight. β-hydroxy carboxylic acid, namely, salicylic acid, or pharmaceutically acceptable salts thereof, is present in the compositions in an amount of from about 0.1% to 15%, preferably, about 0.2% to 10%, more preferably about 0.5 to 2%, by weight; glycerophosphate ester or salt, namely, sodium or calcium glycerophosphate, is present in the compositions in an amount of from about 0.1 % to the solubility limit of the glycerophosphate in the hydroalcoholic composition, typically in the range of about 0.1% to about 2%, preferably, 0.2% to 1%, more preferably about 0.25% to 0.75% by weight.

The pH range of the composition is about 2.5 to about 5.5, preferably about 2.5 to about 4.5, more preferably about 3.3 to about 4.0. Although a cloudy composition, without precipitate, is tolerable, the composition is preferably in solution and clear. It is to be understood that solutions for adjusting pH to the appropriate value, e.g., sodium hydroxide (NaOH) may be added to the compositions of the present invention, as required. For the hydroalcoholic compositions of the invention having an increased alcohol content (e.g., 50% or more), the pH is adjusted appropriately to accommodate the level of alcohol combined with the polyhydric alcohol phosphate or disaccharide polyol phosphate salt, and to achieve a resultant product that is preferably a clear and precipitate-free solution. The final composition of the invention is stable at both low and elevated temperatures, e.g., from about −15° C. to about 55° C. The present composition efficiently reduces the size of blemishes, clears pores, and reduces overall redness after topical application on the skin. Moreover, the stinging and burning sensations often associated with the use of α-hydroxy carboxylic acids are substantially lessened in view of the inclusion of the glycerophosphate ester or salt in combination with the other components and active(s) of the present invention.

As a solvent component of the compositions of the present invention, the alcohol may be a monohydric, dihydric or polyhydric alcohol, such as a $C_2$–$C_6$ alkanol, e.g., ethyl alcohol and isopropyl alcohol and the like. 95% (190 proof) alcohol is particularly suitable for use. Other alcohols, such as polyhydroxy alcohols, such as ethylene or propylene glycol and the like, are also envisioned for use in the present compositions.

As mentioned above, an active component, more particularly, the anti-acne active, in the compositions of the invention is a keratolytic compound. Examples of such compounds include, but are not limited to, β-hydroxy carboxylic acids, particularly, the $C_3$–$C_{15}$, preferably the $C_3$–$C_{10}$, β-hydroxy carboxylic acids and their physiologically acceptable salts, and the α-hydroxy carboxylic acids, particularly, the $C_1$–$C_{25}$ α-hydroxy carboxylic acids and their physiologically acceptable salts. Also as mentioned above, preferred as keratolytic agents are the β-hydroxy carboxylic acids, particularly, salicylic acid, including its alkali metal, e.g., sodium and ammonium salts.

With regard to the α-hydroxy carboxylic acids, nonlimiting examples of these keratolytic compounds for use in the present compositions include, but are not limited to, 2-hydroxyethanoic acid (glycolic acid); 2-hydroxypropanoic acid (lactic acid); 2-methyl 2-hydroxypropanoic acid (methyllactic acid); 2-hydroxybutanoic acid; 2-hydroxypentanoic acid; 2-hydroxyhexanoic acid; 2-hydroxyoctanoic acid; 2-hydroxynonanoic acid; 2-hydroxydecanoic acid; 2-hydroxyundecanoic acid; 2-hydroxydodecanoic acid (α-hydroxylauric acid); 2-hydroxytetradecanoic acid (α-hydroxymyristic acid); 2-hydroxyhexadecanoic acid (α-hydroxypalmitic acid); 2-hydroxyoctadecanoic acid (α-hydroxystearic acid); 2-hydroxyeicosanoic acid (α-hydroxyarachidonic acid); 2-phenyl 2-hydroxyethanoic acid (mandelic acid); 2,2-diphenyl 2-hydroxyethanoic acid (benzylic acid); 3-phenyl 2-hydroxypropanoic acid (phenyllactic acid); 2-phenyl 2-methyl 2-hydroxyethanoic acid (atrolactic acid); 2-(4'-hydroxyphenyl) 2-hydroxyethanoic acid; 2-(4'-chlorophenyl) 2-hydroxyethanoic acid; 2-(3'-hydroxy-4'-methoxyphenyl) 2-hydroxyethanoic acid; 2-(4'-hydroxy-3'-methoxyphenyl) 2-hydroxyethanoic acid; 3-(2-hydroxyphenyl) 2-hydroxypropanoic acid; 3-(4'-hydroxyphenyl) 2-hydroxypropanoic acid; and 2-(2',4'-dihydroxyphenyl) 2-hydroxyethanoic acid. In general, preferred acids are glycolic acid, lactic acid, citric acid and 2-hydroxyoctanoic acid and physiologically acceptable salts thereof.

Without wishing to be bound by a particular theory, the unique presence of the glycerophosphate ester or salt, particularly sodium or calcium glycerophosphate, in accordance with the invention is believed to reduce significantly the irritation of the astringent compositions of the present invention, as well as playing a role in reducing sebum production on the skin.

In addition to the above-described essential ingredients, the compositions of the invention can include a variety of other commonly used ingredients in pharmaceutically and physiologically acceptable forms and amounts to impart additional and/or advantageous properties to the compositions. For example, compounds may be added to provide fragrance to the composition, such as herbal, floral, spice, musk and the like, as well as colorants and/or dyes (e.g., FD&C Yellow #5, 0.1% aqueous solution, in an amount of about 0.04% by weight; FD&C Blue #1, 0.1% aqueous solution, in an amount of about 0.07% by weight). Such additives should be soluble in the hydroalcoholic environment of the composition and should not adversely react with the essential components or other components in the composition. Preferred are water soluble added ingredients. In this regard, the compositions of the present invention may contain various plant/botanical or herbal extracts as added components, typically, hydroglycolic, e.g., in propylene glycol. Suitable botanical extracts may include, but are not limited to camomile extract, aloe barbadensis extract, passion flower extract, cucumber extract, comfrey leaf extract, saponaria officinalis extract, myrrh extract, burdock extract, eucalyptus globulus extract, as well as extracts of rosemary, thyme, sage, bitter orange and coltsfoot, and mixtures thereof. The plant or herbal extract ingredients may be present in the composition in an amount of from about 0.01 to about 0.5%, by weight.

Antimicrobial agents may also be present in the compositions of the present invention. The antimicrobial agents may be compounds typically employed in cosmetic formulations. Nonlimiting examples of such materials include tea tree oil, farnesol, farnesol acetate and benzalkonium chloride In alternative embodiments, the cosmetic compositions of the invention may be provided as cream, ointment, or lotion formulations, or other types of formulations. In cases where nonaqueous formulations are desired, e.g., ointments or anhydrous formulations, other ingredients may be added to assist in achieving the appropriate formulation. Further, other forms of the compositions may be used, such as sticks, roll-on formulations, mousses, aerosol sprays, pad-applied formulations, and overnight facial masks. Peelable facial masks may be formulated by preparing the compositions as a gel or paste. To achieve the latter type of product form, a film-forming polymer (e.g., polyvinyl alcohol) and an adhesion promoting polymer (e.g., hydrophobic acrylate or methacrylate polymer, such as Pemulen TR2® from the B.F. Goodrich Company) are necessary.

The compositions of the present invention may also be formulated to contain emollient materials. Amounts of the emollients may range anywhere from about 0.1 to about 10%, preferably from about 0.5 to 5%, by weight. It will be appreciated by those skilled in the art that water-thin anti-acne products typically contain lower levels of emollients, generally less than 10%, by weight in the compositions.

Examples of suitable ester emollients include, but are not limited to, alkenyl esters of fatty acids having 10 to 20 carbon atoms, of which oleyl myristate, oleylstearate, and oleyl oleate are examples; ether-esters, such as fatty acid esters of ethoxylated fatty alcohols; polyhydric alcohol esters, such as ethylene glycol mono and di-fatty acid esters, diethylene glycol mono- and di-fatty acid esters, polyethylene glycol (200–6000) mono- and all-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty esters, ethoxylated glyceryl monostearate, 1,3-butylene glycol monostearate, 1,3-butylene glycol distearate, polyoxyethylene polyol fatty-acid ester, sorbitan fatty acid esters, and polyoxyethylene sorbitan fatty acid esters; and esters of lower alcohols and fatty acids. More than one emollient may be formulated into the compositions of this invention.

Particularly preferred esters, among those listed above, for use in the compositions of the present invention include PEG-7 glyceryl cocoate, as well as PEG-20 to PEG-80 hydrogenated castor oil, such as PEG-40 hydrogenated castor oil (available as Cremophore RH40®), and also PPG-10-cetyl ether (available as Procetyl®).

In addition to the foregoing ingredients, humectants may be formulated into the compositions of the present invention. Suitable humectants are those of the polyhydric alcohol type. In general, a humectant aids in increasing the effectiveness of the emollient; it may reduce scaling, stimulate removal of built-up scale, moisturize and improve skin feel. Typical polyhydric alcohols include glycerol, glycerin, polyalkylene glycols and alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, 1,2,6-hexanetriol, ethoxylated glycerol, propoxylated glycerol and mixtures thereof. Optimally, the humectant is glycerin. The amount of humectant may range from about 0.1% to 30%, preferably about 0.5% to 5%, by weight of the composition.

Thickeners or viscosifiers in amounts up to about 5% by weight of the composition may also be included for improved spreading effect on the skin. As is appreciated by those having skill in the art, the precise amount of thickener or viscosifier can vary depending upon the consistency and thickness of the final composition which is desired. Exemplary thickeners are xanthan gums, sodium carboxymethyl cellulose, hydroxyalkyl and alkyl celluloses (e.g., hydroxypropyl cellulose) and crosslinked acrylic acid polymers such as those sold by B.F. Goodrich under the Carbopol trademark and those sold by Seppic, SA, France, under the Sepigel trademark. The viscosity of the compositions of the invention will depend upon the final formulations prepared. Accordingly, and as well known to those having skill in the art, the viscosities of the present compositions can therefore range from about 100 to 2000 centistokes for lotions to water-thin for the hydroalcoholic compositions as described.

Physiologically acceptable surfactants, emusifying agents, and/or cleansing agents, as are widely used in cosmetic compositions, may also be included in the present compositions. The compositions of the invention containing suitable ionic, cationic, anionic, zwitterionic, or amphoteric surfactants or cleansing agents in amounts suitable to achieve an effective cleansing function. Suitable surfactants for use are generally known in the art, such as those provided in The International Cosmetic Ingredient Handbook, Third Edition, *Monographs*, Eds. J. A. Wenninger and G. N. McEwen. Jr., Ph.D. J. D., *The Cosmetic, Toiletry and Fragrance Association,* Washington, D.C., e.g., pages 919 et seq., 1995. In accordance with this aspect of the invention, an illustrative formulation is provided in Table 2.

As is further recognized in the art, the active and essential interactive component ingredients, such as β-hydroxy carboxylic acid, e.g., salicylic acid and cosmetically acceptable salts thereof, and the $C_2$–$C_{18}$ polyhydric alcohol phosphate or disaccharide polyol phosphate ester or salt, e.g., calcium glycerophosphate, of the present compositions are formulated in a pharmaceutically acceptable carrier or vehicle. Collectively the alcohol, water, solvents, humectants and/or thickeners, surfactant and other adjuvants or excipients, e.g., fragrance(s) and colorant(s), if present, are viewed as pharmaceutically acceptable carriers for the keratolytic agent and glycerophosphate ester or alkali-metal salt in these compositions. The total amount of carrier will customarily range from about 1 to 99.9%, preferably from about 80 to 99% by weight (for emulsions, about 70% to 80%, by weight).

The cosmetic compositions of the invention can be applied on a daily basis. As a general guide, up to three applications can be made to an area of skin each day. A typical course of treatment can range from about 5 days to 6 months to a year, or until the composition effects a significant reduction in the severity of a skin condition, such as pimples, clogged pores and redness, which are particularly associated with acne vulgaris.

EXAMPLES

The examples as set forth herein are meant to exemplify the various aspects of carrying out the invention and are not intended to limit the invention in any way. Unless otherwise specified, it is to be understood that the concentrations of the component ingredients in the compositions of the invention are in %, w/w, based on the total weight of the composition.

Example 1

Cosmetic compositions formulated in accordance with the present invention are presented in Tables 1 and 2. These compositions serve as illustrative formulations which provides the advantageous features of the invention, namely, mildness to the skin after application; nonirritation to the skin; clearness and nongreasiness upon application (transparent); and quick-drying, particularly when the compositions are preferably formulated as water-thin hydroalcoholic formulations.

The compositions (e.g., Table 1) were generally prepared as described hereinbelow:

In a clean and sanitized stainless steel vessel, which was suitable for blending products comprising alcohol, the batch weight of alcohol was weighed. To the batch vessel containing alcohol, salicylic acid was added, glycerin was next added, and menthol crystals were next added using a lightning mixer with marine propeller. The mixture was blended well to result in a clear and uniform mixture. Water was next added to the batch vessel and the formulation was mixed until clear and uniform. Calcium glycerophosphate was slowly added to the water/alcohol phase and blended well until clear and uniform. This mixture was mixed for about ten minutes. To this mixture, sodium hydroxide solution was added and the pH was adjusted accordingly to a final pH range of preferably 3.3 to 3.7. The mixture was blended until clear and uniform. PEG-40 hydrogenated castor oil was premelted to 30° C.–40° C. until clear. After cooling to 30° C., fragrance was added to the melted PEG-40 hydrogenated castor oil and this mixture was well mixed. The PEG-40/fragrance mixture was then added to the batch mixture and blended well. The botanical extract was premixed and added to the batch slowly and mixed until clear and uniform. The colorants were added to the batch mixture and the color was adjusted, if necessary, prior to filtering the solution and storage of the prepared formulation.

TABLE 1

NON-IRRITATING COSMETIC ASTRINGENT COMPOSITION

| INGREDIENT | %, BY WEIGHT |
|---|---|
| Denatured Alcohol (95%) | 30.00 |
| Water, Deionized | 66.14 |
| Salicylic Acid | 0.52 |
| Calcium Glycerophosphate | 0.50 |
| Sodium Hydroxide (10% aqueous solution) | 0.05 |
| Glycerin | 1.00 |
| Menthol | 0.08 |
| PEG-40 Hydrogenated Castor Oil | 1.00 |
| Fragrance | 0.30 |
| Hydroglycolic Plant Extract | 0.30 |
| Colorant | 0.11 |
| | 100.00% |

TABLE 2

NON-IRRITATING COSMETIC ASTRINGENT COMPOSITION

| INGREDIENT | %, BY WEIGHT |
|---|---|
| Water, Deionized | 57.58 |
| $C_{14}$–$C_{16}$ Olefin Sulfonate (Bioterge AS-40) | 24.00 |
| Lauryl Glucoside and Cocamidopropyl Betaine (TEGO Glucoside L-55; Goldsmidt) | 5.00 |
| Cocamidopropyl Phosphatidyl PG-Dimonium Chloride (Phospholipid PTC) | 4.00 |
| Salicylic Acid | 0.52 |
| Calcium Glycerophosphate | 0.50 |
| Sodium Hydroxide (10% aqueous solution) | 0.05 |
| Glycerin | 3.50 |
| Menthol | 0.05 |

TABLE 2-continued

NON-IRRITATING COSMETIC ASTRINGENT COMPOSITION

| INGREDIENT | %, BY WEIGHT |
|---|---|
| PEG-40 Hydrogenated Castor Oil (Cremophor RH-40) | 1.00 |
| Fragrance | 0.15 |
| Hydroglycolic Plant Extract | 0.45 |
| Butylene Glycol | 3.00 |
| Methylparaben | 0.15 |
| Disodium EDTA | 0.05 |
| | 100.00% |

The compositions of the present invention were evaluated by means of in vitro assays to assess irritancy potential. These assays were employed to compare the irritancy potential of the compositions of the invention relative to that of the commercially-available comparative product. The assays included a bovine corneal opacity and permeability (BCOP) assay, a time course assay using the Epiderm™ skin model bioassay, and a hen's egg test utilizing the chorioallantoic membrane (HET-CAM). The illustrative formulation presented in Table 1 was used in the comparative tests as described in Examples 2–4 hereinbelow.

Example 2

Bovine Corneal Opacity and Permeability Assay (BCOP)

The bovine corneal opacity and permeability assay (BCOP) was used to assess the ocular irritancy of test formulations to isolated bovine corneas. Bovine corneas, obtained as a by-product from freshly slaughtered animals, were mounted in special holders and exposed to the test formulations. An in vitro score was determined for each test material based on the induction of opacity and permeability to fluorescein in the isolated bovine corneas. In these experiments, the potential ocular irritancy of the composition formulated in accordance with the invention and exemplified in Table 1 was compared with that of the commercially-available comparative product. Ocular irritancy was measured by changes in opacity and permeability to fluorescein in isolated bovine corneas. Five corneas were treated with each test material. Based on changes in corneal opacity and permeability relative to control corneas, an in vitro score was determined. In these evaluations, ethanol (95%) was used as a control and is rated as a moderate to severe irritant with an in vitro score range of 56.3 to 65.0.

Materials and Methods

Bovine Eyes and the Preparation of Corneas

Bovine eyes were obtained from a local abattoir as a by-product from freshly slaughtered animals. The eyes were excised and then placed in Hanks' Balanced Salt Solution (HBSS), supplemented with Penicillin/Streptomycin, and transported to the laboratory on wet ice. The corneas were used within 24 hours of receipt.

The tissue surrounding the eyeball was carefully pulled away and the was cornea excised such that a 2 to 3 mm rim of sclera was present around the cornea. The isolated corneas were then stored in a petri dish containing HBSS until they were mounted in a corneal holder. The corneas were grossly examined for damage and those exhibiting defects were discarded. The corneas were mounted in the holders with the endothelial side against the O-ring of the posterior half of the holder. The anterior half of the holder was then positioned on top of the cornea and the screws were tightened. Starting with the posterior compartment, the two compartments of the corneal holder were then filled with Eagle's Minimum Essential Medium (MEM) supplemented to contain 1 % fetal bovine serum (complete MEM). The corneal holders were incubated at 32±1° C. for a minimum of one hour.

Bovine Corneal Opacity and Permeability Assay

After a minimum of one hour of incubation, the corneal holders with the corneas in place were removed from the incubator and the medium was removed from both compartments and replaced with fresh medium. The opacity was determined for each cornea using a Spectro Design OP-KIT opacitometer. Three corneas whose opacity readings were close to the median opacity for all of the corneas were selected as the negative control corneas. The medium was then removed from the anterior part of the holder and replaced with the test formulation or with the positive control. For the negative control corneas, the medium was replaced with fresh complete MEM.

Method for Testing Liquid or Surfactant Materials

Liquids were tested neat. 750 microliters of test material (test formulation or positive control) were introduced into the anterior compartment of the holder while slightly rotating the holder to ensure uniform distribution of the test material over the cornea. The corneas were incubated in the presence of the test material at 32±1° C. for 10 minutes. When the test material was removed, the epithelial side of the cornea was washed at least three times with complete MEM to ensure total removal of the test material. The anterior compartment was refilled with complete MEM and the opacity was determined. The corneas were returned to the incubator for approximately two hours after which a second measure of opacity was obtained. The values obtained at this second measurement were used in calculating the corneal opacity.

After the second opacity measurement was performed, the medium was removed from both chambers of the holder. The posterior compartment was refilled with fresh complete MEM. One ml of a 4 mg/ml fluorescein solution was added to the anterior compartment. The corneas were then incubated in a horizontal position, anterior side up, for approximately 90 minutes at 32±1° C. An aliquot of medium was removed from the posterior chamber and its optical density at 490 nm ($OD_{490}$) was determined using a Milton Roy Spectronic 21D spectrophotometer. If the OD490 of a test or control sample was greater than 0.900, the $OD_{490}$ of a 1:5 dilution of the sample in MEM was determined.

Opacity Measurement

The opacity changes for each cornea (including the negative controls) were calculated by subtracting the initial (pre-treatment) opacity value from the final (post-treatment) opacity value. The opacity changes for the test material-treated corneas were then corrected by subtracting the average opacity change observed for the negative controls. The mean opacity value of each treatment group was calculated by averaging the mean corrected opacity values of the treated corneas for each treatment condition.

Permeability Measurement

The corrected $OD_{490}$ was calculated by subtracting the mean $OD_{490}$ of the negative control corneas from the $OD_{490}$ value of each treated cornea. The mean $OD_{490}$ value of each treatment group was calculated by averaging the corrected $OD_{490}$ values of the treated corneas for that treatment condition. The following formula was used to determine the in vitro score:

$$\text{In Vitro Score} = \text{Mean Opacity Value} + (15 \times \text{Mean } OD_{490} \text{ Value}).$$

The BCOP assay was accepted when the positive control, ethanol, caused an in vitro score that fell within two standard deviations of the historical mean.

Table 3 summarizes the results from the BCOP assay. The opacity, permeability and in vitro score for each test material and the positive control are presented in Table 3. The positive control value met acceptance criteria (the range of values falling within two standard deviations of the mean is 34.8 to 70.0).

The following classification system was established by Sina et al., "A collaborative evaluation of seven alternatives to the Draize eye irritation test using pharmaceutical intermediates", Fundamental and Applied Toxicology 26:20–31, 1995), based on studies with a wide range of test materials. This classification system provides a good initial guide to the interpretation of these in vitro data:

In vitro score:

| | | |
|---|---|---|
| from 0 to 25 | = | mild irritant |
| from 25.1 to 55 | = | moderate irritant |
| from 55.1 and above | = | severe irritant |

TABLE 3

| Test Formulation | Opacity Measurement | Permeability Measurement | In Vitro Score |
|---|---|---|---|
| Composition of Invention (See Table 1) | 22.5 | 0.053 | 23.3 |
| Comparative Product | 56.1 | 0.284 | 60.4 |

As observed from the results presented in Table 3, the in vitro test score in the BCOP test for the composition prepared in accordance with the invention was 23.3, while that for the comparative product was 60.4. Compared with the composition of the invention, the commercially-available comparative product was rated as having severe irritation potential and was similar to the ethanol positive control having a range of 56.3 to 65.0. By contrast, the composition of the invention was rated as having only mild irritation potential and was clearly different from the comparative product formulation.

Example 3

MTT Epiderm™ Skin Model Bioassay

The EpiDerm™ Skin Model Bioassay Kit (MatTek Corporation, Ashland, Mass.) was used to assess the potential skin toxicity of test materials. The MTT (i.e., 3-[4,5-dimethylthiazol-2-yl]-2,5-diphenyltetrazolium bromide) conversion assay, which measures the mitochondrial succinate dehydrogenase-mediated reduction of MTT to a blue formazan precipitate, was used to assess mitochondrial metabolism in cell substrates after exposure to a test formulation for various time periods. The duration of exposure resulting in a 50% decrease in MTT conversion in test formulation-treated EpiDerm™ cultures, relative to control cultures, was determined ($ET_{50}$).

In these assays the potential toxicity of the compositions formulated in accordance with the invention was evaluated and compared with that of the commercially-available comparative product, as measured by the conversion of MTT by EpiDerm™ after exposure to each of the compositions for various time periods. Each formulation was tested in a definitive assay (four or five time periods) to determine the duration of exposure to the test formulations which resulted in the $ET_{50}$ endpoint. The composition as presented in Table 1 was used as an exemplary test formulation of the invention in this study.

Materials and Methods

EpiDerm™ Skin Model Bioassay Protocol

Upon receipt of the EpiDerm™ Skin Bioassay Kit, the solutions were stored as indicated. The EpiDerm™ skin samples were stored at 2–8° C. until used. An appropriate volume of EpiDerm™ assay medium was removed and warmed to approximately 37° C. 0.9 ml of assay medium was aliquoted into the wells of each 6-well plate. The six-well plates were labeled to indicate test formulations and time exposure. The EpiDerm™ samples were inspected for air bubbles between the agarose gel and Millicell insert prior to opening the sealed package. Cultures with air bubbles covering greater than 50% of the Millicell area were not used. The 24-well shipping containers were removed from the plastic bag and their surfaces were disinfected with 70% ethanol. The EpiDerm™ skin samples were transferred aseptically into the 6-well plates. The EpiDerm™ cultures were then incubated at 37±1° C. in a humidified atmosphere of 5±1% $CO_2$ in air for at least one hour. The medium was aspirated and 0.9 ml of fresh medium was added to each assay well below the EpiDerm™. The trays were returned to the incubator until treatment was initiated.

MTT Assay

Four to five time points were tested in duplicate for each test formulation. 100 microliters of the neat liquid test formulation was applied to each EpiDerm™ construct. Two EpiDerm™ constructs were used for each of three time points for the exposure time controls (negative control). Those cultures designated as exposure time controls received 100 $\mu$l of sterile deionized water. Duplicate cultures of the positive control (1 % Triton X-100) were tested at two exposure times of 4 and 8 hours. The plates were then incubated for the approximate amount of time.

A 1.0 mg/ml solution of MTT in warm Dulbecco's Modified Eagle's Medium (DMEM) was prepared and the solution was filtered through a 0.45 $\mu$m filter to remove undissolved crystals. After the appropriate exposure time, the EpiDerm™ skin cultures were extensively rinsed with Dulbecco's Phosphate Buffered Saline (DPBS) and the wash medium was decanted. 0.3 ml of MTT reagent were added to wells in a prelabeled 24-well plate. The EpiDerm™ skin samples were transferred to the appropriate wells after rinsing. The trays were incubated at 37±° C. for approximately three hours in a humidified atmosphere of 5±1% $CO_2$ in air.

After the incubation period with MTT solution, the EpiDerm™ skin samples were extensively rinsed with DPBS, cleared of excess liquid, and transferred to a prelabeled 24-well plate containing 2.0 ml of isopropanol. The plates were stored in the refrigerator (2–8° C.) until the last exposure time was harvested. The plates were then shaken for two hours at room temperature.

At the end of the extraction period, the liquid within the millicell inserts was decanted into the well from which the millicell insert was taken. The extract solution was mixed and 200 μl were transferred to the appropriate wells of a 96-well plate. The absorbance at 550 nm ($OD_{550}$) of each well was measured with a Molecular Devices (Menlo Park, Calif.) Vmax plate reader.

The mean $OD_{550}$ values of the exposure time control wells, blank control wells, positive control wells and each test formulation well for the various exposure times were calculated. The corrected mean $OD_{550}$ values of the exposure time control, test formulation exposure times and the positive control exposure times were determined by subtracting from each the mean $OD_{550}$ values for the blank control. The raw absorbance values were captured, and the following calculations were made:

$$\%\text{ of Control} = \frac{\text{corrected mean } OD_{550} \text{ of Test Formulation Exposure time}}{\text{corrected mean } OD_{550} \text{ of Exposure time Control}} \times 100\%$$

Time response curves were plotted using Lotus 1-2-3 with the % of control on the ordinate and the test article exposure time on the abscissa. The $ET_{50}$ was interpolated from each plot. The assay results were accepted if the $ET_{50}$ value 0 of the positive control fell within two standard deviations of the historical mean.

A minimum of four time points were tested in duplicate for each test formulation. The exposure times for the test composition of the invention was 1, 4, 8 and 16 hours; the exposure times for the comparative product were 1, 2, 4 and 8 hours. The exposure time control was also tested in duplicate at 4, 16 and 24 hours. Table 4 summarizes the $ET_{50}$ results of the EpiDerm™ assays for the test formulations and the positive control. The time response curves for the test formulations are shown in FIG. 1. The $ET_{50}$ value for the positive control, Triton X-100 (1 %), fell within two standard deviations of the historical mean (4.9 to 6.54 hours), thereby meeting the acceptance criteria.

TABLE 4

| Test Formulation | $ET_{50}$ (hours) |
|---|---|
| Composition of Invention (see Table 1) | 11.3 |
| Comparative Product | 1.4 |
| Triton X-100 (1%) | 5.7 |

The MTT Epiderm™ skin model bioassay for skin irritation potential compares the estimated time to a 50% reduction in mitochondria metabolism ($ET_{50}$). The shorter the $ET_{50}$, the higher the irritation potential. The $ET_{50}$ measured for the composition of the invention was 11.3 hours (Table 4), while the commercially-available comparative product had an $ET_{50}$ of 1.4 hours. Thus, the composition of the invention demonstrated significantly less skin irritation potential than the comparative product preparation.

Example 4

The Hen's Egg Test—Utilizing the Chorioallantoic Membrane (HET-CAM)

To evaluate the composition of the invention for ocular irritancy potential and to compare the results with the commercially-available comparative product, the HET-CAM test was employed. This test is a modification of that described by F. H. Kemper and N. P. Leupke, 1986, "The HET-CAM Test: An Alternative to the Draize Test", FD Chem. Toxic., 24:495–496.

The chick embryo has been used extensively in toxicology. As taught in J. Leighton et al., 1985, "Macroscopic Assay of Focal Injury in the Chorioallantoic Membrane", In: *Alternative Methods in Toxicology,* 3, In vitro Toxicology E2, pp. 357–369, Alan M. Goldberg, Ed., Mary Ann Liebert Publishers, Inc., New York, the chorioallantoic membrane (CAM) of the chick embryo is a complete tissue with organoid elements from all germ cell layers. The chorionic epithelium is ectodermal and the allantoic epithelium is endodermal. The mesoderm located between these epithelia is a complete connective tissue including arteries, capillaries, veins and lymphatic vessels. The CAM responds to injury with a complete inflammatory reaction, comparable to that induced in the rabbit eye test. It is technically easy to study, and is without nerves to sense pain.

To carry out the HET-CAM, fresh, fertile, White Leghorn eggs were obtained from Avian Services in Frenchtown, N.J. The eggs were stored at this facility for up to 7 days, at 13° C., before being incubated. For incubation the eggs were placed on their sides in a Kuhl incubator, which rotates the eggs once every hour. The temperature was controlled at 99° F. (±1°) with a relative humidity of 60–70% for the 10 days of incubation. On day 8 the eggs were turned so that the acutely-angled end faced down.

On day ten 10, each egg was removed from the incubator and placed in a Plexiglass work enclosure, which had been preheated and humidified so that its environment approached that of the incubator. A cut was made in the larger end of each egg where the air sack is located. A Dremel® Moto-Flex Tool (model 232-5) equipped with a Dremel® Cut-Off Wheel (No. 409) was used to make each cut. Forceps were then used to remove the shell down to the shell-membrane junction. The inner egg membrane was then hydrated with warm, physiological saline solution. The saline was removed after a 2 to 5 minute exposure. Utilizing pointed forceps, the inner egg membrane was then carefully removed to reveal the CAM.

The test or reference composition, at a dosage of 0.3 ml of a liquid (or 0.3 g of a solid) was then administered to each of 4 CAMs. Twenty seconds later, the test or control composition was rinsed from each CAM with 5 ml of physiological saline. All CAMs were observed immediately prior to the administration of the test composition and at 30 seconds, 2 minutes and 5 minutes after exposure to the test composition. Because the CAM of the hen's egg has been shown to be more sensitive to irritants than is the rabbit's eye, dilutions of the test and reference compositions were used. The reactions of the CAM, the blood vessels, including the capillaries, and the albumin were examined and scored for irritant effects as presented below:

| | Score Time (min.) | | |
|---|---|---|---|
| Effect | 0.5 | 2 | 5 |
| Hyperemia | 5 | 3 | 1 |
| Minimal Hemorrhage ("Feathering") | 7 | 5 | 3 |

-continued

| Effect | Score Time (min.) 0.5 | 2 | 5 |
|---|---|---|---|
| Hemorrhage (Obvious Leakage) | 9 | 7 | 5 |
| Coagulation and/or Thrombosis | 11 | 9 | 7 |

The numerical time-dependent scores were totaled for each CAM. Since each reaction type can be recorded only once for each CAM, the maximum score per CAM is 32. The mean score was determined for all CAMs similarly tested. The results of this comparative test are presented in Table 5.

TABLE 5

| | CAM # | Score at 0.5 min. | 2 min. | 5 min. | Total |
|---|---|---|---|---|---|
| Test Composition | | | | | |
| Composition of Invention, (50%) | 1 | 0 | 0 | 1 | 1 |
| | 2 | 0 | 3 + 5 | 0 | 8 |
| | 3 | 0 | 3 | 0 | 3 |
| | 4 | 5 | 0 | 0 | 5 |
| | | | | Average: | 4.25 |
| Comparative Product, (50%) | 1 | 5 + 7 | 0 | 5 | 17 |
| | 2 | 0 | 3 + 5 | 5 | 13 |
| | 3 | 5 + 7 | 0 | 0 | 12 |
| | 4 | 5 + 7 | 0 | 0 | 12 |
| | | | | Average | 13.50 |

Each test composition was classified as indicated in the following:

| Mean Score | Irritation Potential |
|---|---|
| 0.0–4.9 | Practically none |
| 5.0–9.9 | Slight |
| 10.0–14.9 | Moderate |
| 15.0–32.0 | Severe |

The reference composition used in the HET-CAM assays has historically been categorized as being moderately irritating, eliciting scores approaching 15, at 24 hours, when dosed neat and tested using the Draize ocular irritation methodologies. Under the conditions of this test, the results of the HET-CAM indicate that the sponsor-submitted product has virtually no ocular irritation potential, compared with the reference article and the commercially-available comparative product.

In sum, the cumulative results of the in vitro tests indicated that the compositions of the present invention were mild and nonirritating. The mildness and nonirritating properties of the present compositions attest to its superior performance when used in the irritancy assays and compared with a commercially-available comparative product.

The contents of all patents, patent applications, published articles, abstracts, books, reference manuals, dictionaries and indexes cited herein are hereby incorporated by reference in their entirety to more fully describe the state of the art to which the invention pertains.

As various changes can be made in the above-described subject matter without departing from the scope and spirit of the invention, it is intended that all subject matter contained in the above description, shown in the accompanying drawings, or defined in the appended claims will be interpreted as descriptive and illustrative, and not in a limiting sense. Many modifications and variations of the present invention are possible in light of the above teachings. It is therefore to be understood that within the scope of the appended claims, the invention may be practiced otherwise than as specifically described.

What is claimed is:

1. A topical skin treatment composition for reducing the severity of adverse skin conditions, comprising, by weight of the composition:

(a) from about 0.1% to 15% of a β-hydroxy carboxylic acid selected from the group consisting of salicyclic acid and physiologically acceptable salts thereof;

(b) a phosphate ester as a salt complex of a monovalent sodium or ammonium ion present in the composition in an amount effective to reduce irritation and selected from the group consisting of sodium glycerophosphate and ammonium glycerophosphate;

(c) from about 5% to about 55% alcohol, said alcohol being selected from the group consisting of monohydric alcohols, dihydric alcohols and polyhydric alcohols having from 2 to 6 carbon atoms; and (d) from about 50% to about 95% water, said composition having a pH of from about 2.5 to about 4.5.

2. The composition of claim 1 wherein the water is present in an amount of from about 60 to 80%.

3. The composition of claim 1 wherein the alcohol is present in an amount of from about 15 to 40%.

4. The composition of claim 1, wherein the phosphate ester is present in the composition in an amount of from about 0.1% to about the solubility limit of the glycerophosphate in the composition.

5. The composition of claim 5 wherein the glycerophosphate is sodium glycerophosphate and is present in an amount of from about 0.1 to 2%.

6. The composition according of claim 1 wherein the alcohol is selected from the group consisting of ethyl alcohol, isopropyl alcohol, ethylene glycol, and propylene glycol.

7. The composition of claim 1 further comprising an ingredient selected from the group consisting of emollients, antimicrobials, humectants, surfactants, fragrances and colorants.

8. The composition of claim 5 wherein the β-hydroxy carboxylic acid is salicylic acid.

9. The composition of claim 8 wherein the pH is in the range of about 3.3 to about 4.

10. A method for diminishing the severity of an adverse skin condition comprising applying to the skin an effective amount of the composition according to claim 1 or 4.

11. The method of claim 10 wherein the β-hydroxy carboxylic acid is salicylic acid.

12. The method of claim 10 wherein the skin condition is acne vulgaris.

13. The composition of claim 1, wherein the monovalent ion is sodium.

14. The composition of claim 1, wherein the pH is in the range of about 3.3 to about 4.0.

15. A method for diminishing the severity of an adverse skin condition, including blemishes and redness, comprising:

(A) providing a composition comprising by weight of the composition:

(a) from about 0.1% to 15% of a β-hydroxy carboxylic acid selected from the group consisting of salicyclic acid and physiologically acceptable salts thereof;

(b) a phosphate ester as a salt complex of a monovalent sodium or ammonium ion present in the composition in an amount effective to reduce irritation and selected from the group consisting of sodium glycerophosphate and ammonium glycerophosphate;

(c) from about 5% to about 55% of a mono-, di-, or polyhydric alcohol having from about 2 to about 6 carbon atoms, and (d) from about 50% to about 96% water, said composition having a pH of from about 2.5 to about 4.5; and (B) topically applying to the skin an effective blemish and redness diminishing amount of the composition of step (A).

16. The method of claim 15 wherein the skin condition is acne vulgaris.

17. The method claim 15, wherein the glycerophosphate ester is present in an amount from about 0.1% to about the solubility limit of the glycerophosphate in said composition.

18. The method of claim 15 wherein the alcohol is selected from the group consisting of ethyl alcohol, isopropyl alcohol, ethylene glycol and propylene glycol.

19. The method of claim 10, 15, 16 or 17 wherein the topical application is on a daily basis.

20. A method of reducing irritancy associated with topical application of a skin composition containing salicylic acid by incorporating into a topical skin formulation a phosphate ester as a salt complex of a monovalent sodium or ammonium ion selected from the group consisting of sodium glycerophosphate and ammonium glycerophosphate present in the composition in an amount effective to reduce irritancy, said composition having a pH of from about 2.5 to about 4.5.

21. The method of claim 20 wherein the glycerophosphate salt is sodium glycerophosphate.

22. The method of claim 20 or 21 wherein the irritancy reducing amount of said phosphate ester in the formulation is from about 0.1% to about 2% by weight of the composition.

23. The method of claim 20 or 21 wherein the irritancy reducing amount of said phosphate ester in the formulation is from about 0.2% to about 2% by weight of the composition.

24. The method of claim 15 or claim 20, wherein the monovalent ion is sodium.

25. The method of claim 17 or claim 22, wherein the pH of the composition is in the range of about 3.3 to about 4.0.

* * * * *